United States Patent [19]

Azoulay

[11] 4,081,557

[45] Mar. 28, 1978

[54] PROTEIN ENRICHMENT OF MAIZE, CASSAVA AND OTHER STARCHY PRODUCTS BY DIRECT FERMENTATION

[75] Inventor: Edgard Elie Yves Azoulay, Marseilles, France

[73] Assignee: Adour Entreprise, Pau, France

[21] Appl. No.: 731,554

[22] Filed: Oct. 12, 1976

[30] Foreign Application Priority Data

Oct. 20, 1975 France .................................. 75 32010

[51] Int. Cl.² ............................. A23J 1/00; A23J 1/14
[52] U.S. Cl. ........................................ 426/18; 426/52; 426/60; 195/28 R
[58] Field of Search ..................... 426/49, 52, 53, 60, 426/44, 48, 18; 195/31 R, 28 R

[56] References Cited

U.S. PATENT DOCUMENTS

| | | | |
|---|---|---|---|
| 2,764,487 | 9/1956 | Wickerham et al. | 426/60 |
| 3,810,997 | 5/1974 | Chien | 426/49 X |
| 3,937,654 | 2/1976 | Solomons et al. | 426/60 X |
| 3,958,015 | 5/1976 | Gay | 426/52 X |

*Primary Examiner*—Raymond N. Jones
*Assistant Examiner*—R. A. Yoncoskie
*Attorney, Agent, or Firm*—Stevens, Davis, Miller & Mosher

[57] ABSTRACT

Products rich in starch and poor in proteins such as maize and cassava are enriched in protein by fermentation with an appropriate yeast such as Candida Tropicalis.

4 Claims, 1 Drawing Figure

U.S. Patent
March 28, 1978
4,081,557
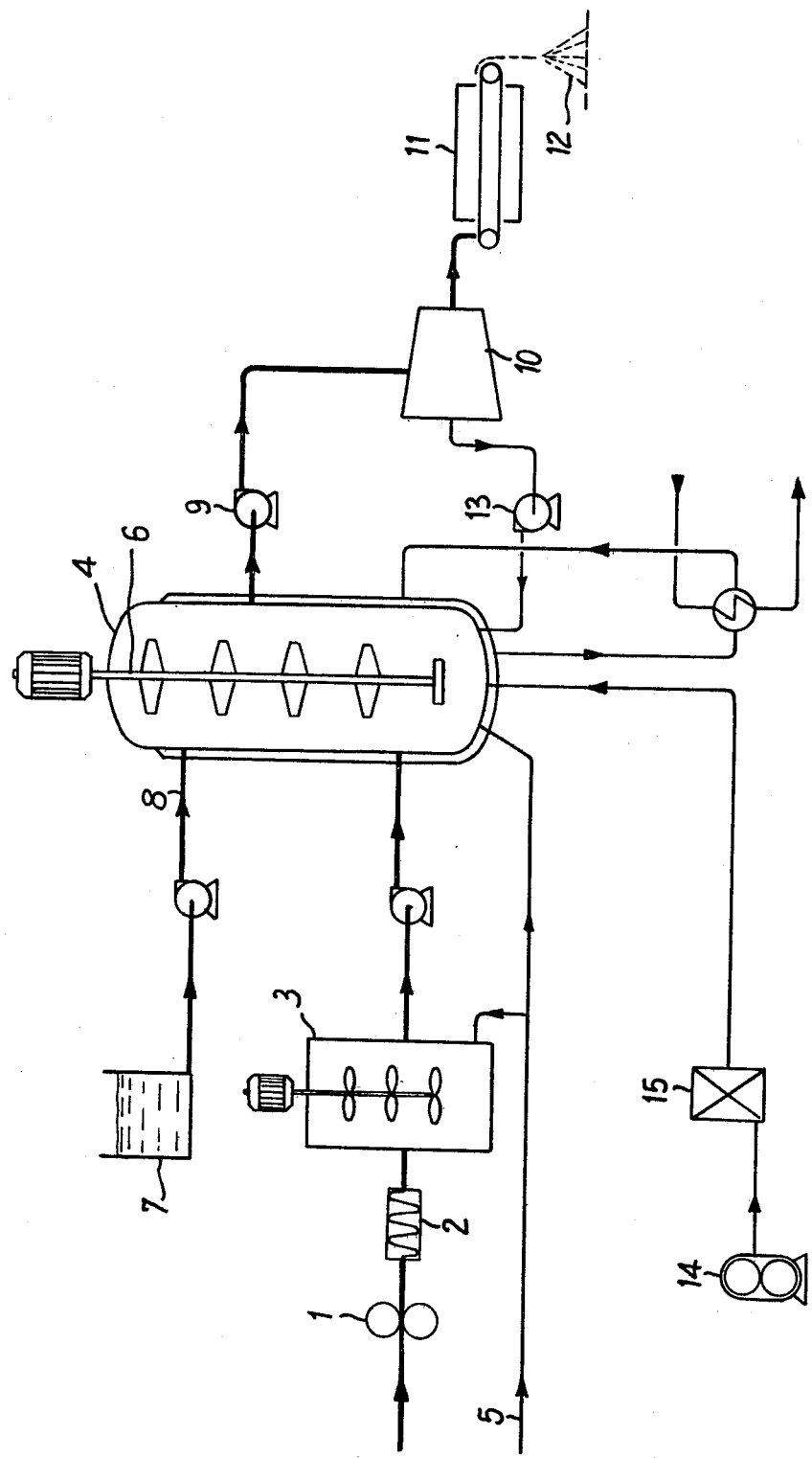

PROTEIN ENRICHMENT OF MAIZE, CASSAVA AND OTHER STARCHY PRODUCTS BY DIRECT FERMENTATION

The invention relates to a process for the protein enrichment, by direct and continuous fermentation, of products which are rich in starch and poor in proteins. The said products can be grains of cereals such as wheat, maize, barley, sorghum, millet, rice, oats or cassava roots, or tubers of potato, yam and the like.

The object is to enrich these products in proteins with a view to their direct use as a balanced foodstuff for animal nutrition and possibly for human nutrition.

The invention more particularly relates to the protein enrichment of maize powder and cassava powder by direct fermentation under the action of selected strains of CANDIDA TROPICALIS YEASTS without it being necessary to subject these carbon-containing substrates beforehand to an exogenous chemical or enzymatic hydrolysis.

Numerous publications describe processes for the protein enrichment of starchy products or waste material of starchy products, such as MAIZE or POTATO, by fermentation by means of certain yeasts such as CANDIDA UTILIS, TORULA, PENICILLIUM and FUSARIUM. These various processes start from products or waste material which contain starch and always comprise either an acid hydrolysis at a pH of about 1.8 or an enzymatic hydrolysis brought about by amylases or by microorganisms chosen because they efficiently provide amylases, such as ASPERGILLUS NIGER, RHIZOPUS, ENDOMYCES, ENDOMYCOPSIS FIBULIGER and SACCHAROMYCES DIASTATIUS, as is evidenced by the following references:

1. E. R. KOOI and F. C. ARMBRUSTER, Production and Use of Dextrose.
   STARCH: Chemistry and Technology, volume 11, page 553, Academic Press 1967.
2. Kurl JARL, Utilisation of Waste materials by fermentation.
   71 Socker-Handlingar, vol. 25 (1971) No. 2, pages 4–11.
3. Anna IKONOMOVA, Use of waste products from the Starch and Glucose Industry for the production for feed purposes.
   ZHIVOTNOVUDNI NAUK 9 (7) 21 28 (1972).
4. F. DESCHAMPS and F. MEYER (Institut National de Recherche Chimique Appliquee) — French Patent No. 74/31,589, Sept. 18, 1974.
5. K. JAROSZ et al. Fermentation of starchy raw materials. PRACE INSTITUTE: LAB. BAD. PRZEM. SPOZ (1974) 24, 1 pp. 7–16.

On the other hand, the fermentation of CASSAVA, another starchy product, has hitherto been carried out discontinuously, either on cassava converted to the condition of a moist solid or on cassava in suspension, using the action, not of YEAST, but of FUNGI of the type of R.HIZOPUS, NEUROSPORA, ASPERGILLUS and MUCOR, as is evidenced by the following references:

6. W. R. STANTON and A. J. WALLBRIDGE (The SECRETARY of STATE for DEFENCE), British Patent No. 1,277,002.
7. W. E. TREVELYAN, Trop. Sci. 16,4 (1974).
   The enrichment of CASSAVA with proteins by moist solid fermentation.
8. A. E. READE and K. F. GREGORY
   Appl. Microb. Vol. 30, No. 6, 897, Dec. 1975.
   High temperature production of proteins enriched feed of CASSAVA by Fungi.
9. K. F. GREGORY et al.
   FOOD TECHNOLOGY, Vol. 30, No. 3, Mar. 30, 1976.
   Conversion of CARBOHYDRATES to PROTEINS by HIGH TEMPERATURE FUNGI.

The process according to the invention differs from the known processes in that:

The starting material is a POWDER or flour, rich in starch, which has been brought into SUSPENSION.

The fermentation employs, in place of filamentous fungi, YEASTS which are known to have a higher protein content and shorter growth times, specifically yeasts of the TROPICALIS type, which are very vigorous, develop on numerous carbon-containing substrates and have been proved to be harmless by numerous foodstuff tests (Arch. Mikrobiol 72-135-139: 1970).

The yeast is used directly in the nutrient medium containing the powder in homogeneous suspension, WITHOUT PRIOR HYDROLYSIS.

The fermentation is carried out in a CONTINUOUS culture with control of the degree of dilution which, at a controlled temperature and controlled pH, conditions the development of the yeast and the enrichment of the product, so that the productivity of the process is greater than the productivity of the fermentations which have been described and which are discontinuous.

The fermentation is not taken to the point of exhaustion of the carbon-containing substrate but is carried out in such a way as to give a dry mixture of residual substrate and yeasts which have a protein content exceeding 15%.

The product obtained after desiccation is a so-called enriched flour containing more than 15% of proteins and ready for human or animal consumption.

According to a first embodiment of the invention, the process of protein enrichment of the maize grain powder comprises four major stages:

1. Selection of the strains of CANDIDA TROPICALIS used in the fermenter.
2. Grinding the maize grains, cassava shavings or other starchy products and bringing them into suspension.
3. Direct and continuous fermentation.
4. Extraction and desiccation of the product consisting of the biomass and residual maize, cassava or other starting product.

SELECTION OF THE STRAINS

An essential characteristic of the invention concerns the culture of the selected microorganisms required for the fermentation, their use in the process and their recovery.

Starting from strains of Candida Tropicalis (CT 101), clones were isolated on nutrient media containing soluble starch as the only source of carbon. These have been indexed under numbers Ct 1001, CT 101/1, CT 101/9 and CT 101/AR.

In addition to the soluble starch, the nutrient medium contains inorganic salts, oligo-elements, growth factors in the form of yeast extract, and an ammoniacal source of nitrogen, in the following proportions:

| | |
|---|---|
| $MgSO_4 \cdot 7H_2O$ | 2 g |
| NaCl | 1 g |
| $NH_4Cl$ | 25 g |

| | |
|---|---|
| -continued | |
| KH$_2$PO$_4$ | 70 g |
| Solution of oligo-elements (Fe, Ni, Co and Cu) | 100 ml |
| Yeast extract known under the trademark DIFCO | 1 g |

It is found that strain CT 1001 develops on soluble starch in a discontinuous culture with a yield, by weight, of 46 g of dry cells formed per 100 g of starch used, representing a yield of 46%, and a growth ratio of 0.75 per hour. The optimum development temperatures are between 30° C and 39° C and above 40° C no development is possible. Under these conditions, the ammonia or the NH$_4$ ion constitutes a source of nitrogen. The pH range which permits best development is between 4 and 6, preferably 4.5 to 5.5. The two growth parameters, namely yield and growth ratio, vary very little with the substrate concentration in the culture medium if the aeration conditions are perfect; these remarks apply up to a starch concentration of 8g/liter.

Under the experimental conditions which permit development on the starch, it is found that the carbon medium only contains a very small amount of glucose liberated by hydrolysis of the starch, corresponding to about 1%. This strain of yeast can thus be considered as developing directly on starch and not on the hydrolysis products liberated beforehand.

The three other strains of Candida Tropicalis selected from strain CT 101 behave like strain CT 1001.

By comparison, on glucose as the sole source of carbon, the growth yield of CANDIDA TROPICALIS is between 50 and 55%, with a growth ratio of 0.80 per hour.

GRINDING AND BRINGING INTO SUSPENSION

The maize grains or cassava shavings or other starchy products are ground in an ordinary grinder, for example a knife-type grinder, to give a powder or flour wherein the size of the grains does not exceed 1 mm and can be as small as 100 microns.

The ground MAIZE grains are brought into suspension in a normal sulphuric acid solution. At this normality, the acid only causes negligable hydrolysis of the starch contained in the maize powder. The homogenized suspension is introduced into the fermenter in such a way that the concentration of maize powder has a value of between 2 g and 200 g/liter.

The ground CASSAVA shavings can be introduced directly into the fermenter without being brought into suspension beforehand.

FERMENTATION EXAMPLE

The culture is carried out in a continuous fermenter of useful capacity 4 liters, with the following values of the parameters of the continuous culture:

Temperature: 32° C
Agitation: vigorous
Aeration: 30 volumes/volume.hr. (volume of air per volume of medium and per hour)
pH adjusted to 5.1 by continuous and controlled addition of N/10 NaOH
Flow rates F#at the inlet and outlet of the reactor controlled simultaneously and to the same values, namely 0.2 liter/hour and 0.4 liter/hour in the case of maize, depending on the type of experiment carried out, while the flow rates F chosen for cassava were 1 liter/hour and 1.5 liters/hour.

Accordingly, the dilution ratio varies from 0.05 per hour to 0.1 per hour for maize and from 0.25 to 0.37 per hour for cassava (useful volume of the fermenter: 4 liters).

The nutrient medium is sterilized at 110° C for 1 hour before introduction into the fermenter.

The innoculum consists of 1 liter of culture medium containing soluble starch inoculated beforehand with the strain of Candida Tropicalis CT 1001 used in the majority of the experiments described, and incubated for 24 hours to give, prior to use, an optical density equal to 1.2 cell concentration units (determined by nephelometry at 450 nm and calculated from calibration curves).

The maize suspension is continuously agitated vigorously and introduced into the fermenter under as nearly as possible perfect conditions of homogeneity, to increase the substrate/microorganism contacts and achieve efficient degradation of the carbon-containing substrate used.

In the case of CASSAVA, the CASSAVA flour is introduced directly into the fermenter without having been brought into suspension beforehand.

ISOLATION OF THE PRODUCT

The product is recovered by centrifuging, dessication at 60° C and conversion to a powder, on which the analytical operations (determination of C, N, starch and proteins) are carried out.

EXAMPLE OF ENRICHMENT OF MAIZE

The following examples of the enrichment of maize are given without implying a limitation to illustrate the invention. Four series of experiments were carried out at flow rates F equal to 0.2 and 0.4 liters/hour. The results are shown in Table 1.

Table I

| Examples | Sampling time | Sample taken | Dry weight of biomass collected | % Nitrogen | % Proteins | % biomass recovered |
|---|---|---|---|---|---|---|
| Number 1 | | | | | | |
| medium containing 2 g/ liter of maize powder | 0 h | 5 ml | 10 mg | 1.4 | 8.8 | — |
| F: 0.2 liter/hour | 11 h | 5 ml | 8.5 mg | 2.7 | 17 | |
| F: 0.4 liter/hour | 16 h | 5 ml | 8.2 mg | 3.8 | 23 | |
| | 20 h | 5 ml | 7.6 mg | 2.7 | 17 | |
| | end of culture | 10 liters | 14.8 g | 3.4 | 21 | 74 |
| Number 2 | | | | | | |
| medium containing 2 g/ liter of maize powder | end of culture | 4 liters | 4.76 g | 3.8 | 24 | 60 |
| F: 0.2 liter/hour | | | | | | |
| Number 3 | | | | | | |

Table I-continued

| Examples | Sampling time | Sample taken | Dry weight of biomass collected | % Nitrogen | % Proteins | % biomass recovered |
|---|---|---|---|---|---|---|
| as above | end of culture | 5 liters | 5.93 g | 3.7 | 23 | 59 |
| Number 4 medium containing 1 g/ liter of maize powder | end of culture | 8.5 liters | 5.42 g | 3.2 | 20 | 64 |

Examination of Table 1 shows that a fraction of the maize powder has been converted to yeasts. The protein content of the biomass collected is calculated from the nitrogen determined by the NESSLER method after mineralization of the cells. It is of the order of 20%. By comparison, the protein content of the yeasts (CT 1001) cultured normally on glucose or soluble starch is from 50% to 60%. The result of the fermentation manifests itself in an overall balance which amounts to a loss of dry matter of the order of 20% to 40% depending on the experimental conditions, and to a protein content which changes from 8 to 9% in the initial maize to values of between 20 and 24% in the final dry matter.

For a flow rate F of 0.4 liter/hour, the biomass recovered corresponds to about 70% of the maize powder introduced, with protein contents of between 18 and 20%. By varying the dilution ratio, the protein contents of the mixture as well as the degree of recovery of the mixture after conversion can be varied.

Table 2 gives the comparative analysis of the initial maize and of the maize enriched by the process described by the invention.

Table 2

|  | Initial ground maize | Maize enriched by fermentation |
|---|---|---|
| Moisture | 10.0% | 10.0% |
| Nitrogen | 1.4% | 3.3% |
| Proteins | 8.75% | 20.6% |
| Carbon | 42.1% | 40.8% |
| Starch | 66.0% | 44.7% |
| Lysine | 3.3 | 6.8 |
| Methionine | 2.2 | 2.9 |
| Cystine | 1.9 | 2.6 |

EXAMPLES OF ENRICHMENT OF CASSAVA

The following examples of enrichment of cassava are given without implying a limitation in order to illustrate the invention. Table 3 below presents the results corresponding to two fermentation examples carried out at flow rates F of 1 liter and 1.5 liters/hour, corresponding to dilution ratios D (and growth ratios) equal to 0.25 and 0.37 per hour, using a suspension in the fermenter which contains 10 g of cassava powder per liter.

Table 3

| Examples | Sampling time | Sample taken | Dry weight of biomass collected | % Nitrogen | % Proteins | % biomass recovered |
|---|---|---|---|---|---|---|
| NUMBER 1 F: 1.5 liters/hour 10 g/liter of cassava | end of culture | 5 liters | 5.6 g | 2.7 | 16.9 | 56 |
| NUMBER 2 F: 1 liter/hour 10 g/liter of cassava | end of culture | 5 liters | 4.2 g | 3 | 18.8 | 42 |

Examination of this table shows that the CASSAVA powder is more completely converted than the maize powder, the percentage of biomass recovered being lower, with a protein content changing, from about 3% to 18%, and with the number of cells varying from $10^{10}$ to $10^{11}$ cells per liter of culture.

Table 4 gives the comparative analysis of the initial CASSAVA and of the CASSAVA enriched by the process described by the invention.

Table 4

|  | Initial cassava | Enriched cassava |
|---|---|---|
| Nitrogen | 0.5% | 3% |
| Proteins | 3.1% | 18% |
| Lysine | 1.1 | 7.7 |
| Methionine | 0.7 | 2.7 |
| Cystine | 0.5 | 2 |

It is found that the product contains more than 15% of proteins, the remainder being cassava depleted in starch. The proportion of yeasts contained in the product can obviously be increased by taking the fermentation of the starch, contained in the cassava, further.

PROCESS

The attached FIGURE schematically represents the industrial device for continuous fermentation.

The MAIZE grains pass into the grinder 1 where they are reduced to a fine powder which, by means of the conveyor 2, enters the tank 3, which serves for the preparation of the suspension. This tank 3, as well as the fermenter 4, are fed with water through the pipeline 5. The suspension is fed into the fermenter 4, equipped with a vigorous mechanical stirrer 6. The fermenter is fed with mineral medium coming from the tank 7, through the pipeline 8. The fermenter can be cooled by circulating a fluid through its double jacket. The product resulting from the fermentation is removed at 9, centrifuged at 10 and dried at 11. The protein-rich maize flour is stored at 12.

The water issuing from the centrifuge is recycled into the fermenter through 13. The air required for the fermentation is fed in by a compressor 14, through a filter 15.

In the case of CASSAVA, the tank 3 for preparing the suspension can be omitted and the CASSAVA powder can be introduced directly into the fermenter.

THE PRODUCT

The invention embraces both the product obtained according to the fermentation process described above and its applications as maize flour or cassava flour which has been balanced in proteins and can be used directly in human or animal nutrition.

In fact, the enriched maize flour contains more than 15% of proteins or more precisely from 15% to 30% by weight of proteins. This flour consists of a mixture containing 70 to 90% by weight of maize depleted in starch and therefore slightly enriched in proteins, and 10 to 30% by weight of yeasts, rich in proteins, resulting from the fermentation of the starch.

In the same way, the enriched cassava flour contains at least 15% of proteins or more precisely from 15 to 30% by weight of proteins. This flour consists of a mixture containing 60 to 80% by weight of cassava depleted in starch and therefore slightly enriched in proteins, and 20 to 40% by weight of yeasts, rich in proteins, resulting from the fermentation of the starch.

I claim:

1. Process for the protein enrichment of products rich in starch, which comprises
   a. grinding maize or cassava to form a powder the grains of which are smaller than 1 mm,
   b. bringing the powder into suspension,
   c. adding inorganic salts, a source of nitrogen, oligo-elements and growth factors to the suspension so as to constitute a complete nutrient medium,
   d. subjecting the nutrient medium to a direct and continuous fermentation with Candida Tropicalis yeast without a prior chemical or enzymatic hydrolysis of said maize or cassava, the said fermentation being carried out with vigorous stirring and vigorous aeration at a pH of between 4 and 6 and at a temperature of between 30° and 39° C, and
   e. recovering the resulting biomass by centrifuging and dessicating it to give a directly consumable flour rich in proteins.

2. Process according to claim 1, in which the fermentation is so carried out as to consume a fraction of the starch containing starting product and to give a product consisting of a mixture of yeasts and of residual initial product, in which the overall content of proteins exceeds 15%.

3. Process according to claim 2, in which the final product has a protein content between 15 and 30%.

4. Process according to claim 1, in which the fermentation is carried out with a strain of yeast CT 1001 selected from CANDIDA TROPICALIS 101 strains obtained by culturing on soluble starch in a nutrient medium containing inorganic salts, oligo-elements, growth factors and a source of nitrogen, the pH of the medium being kept at between 4.5 and 5.5 by means of an aqueous solution of an alkali metal hydroxide, the temperature of the medium being maintained at between 30 and 39° C, and the said medium being subjected to vigorous stirring and vigorous aeration.

* * * * *